United States Patent
Miyauchi et al.

(10) Patent No.: US 12,130,250 B2
(45) Date of Patent: Oct. 29, 2024

(54) FAILURE PREDICTION SYSTEM

(71) Applicant: KYB CORPORATION, Tokyo (JP)

(72) Inventors: Yuki Miyauchi, Kanagawa (JP); Shun Ohuchida, Kanagawa (JP)

(73) Assignee: KYB Corporation, Tokyo (JP)

( * ) Notice: Subject to any disclaimer, the term of this patent is extended or adjusted under 35 U.S.C. 154(b) by 130 days.

(21) Appl. No.: 17/918,513

(22) PCT Filed: Mar. 22, 2021

(86) PCT No.: PCT/JP2021/011822
§ 371 (c)(1),
(2) Date: Oct. 12, 2022

(87) PCT Pub. No.: WO2021/210353
PCT Pub. Date: Oct. 21, 2021

(65) Prior Publication Data
US 2023/0147470 A1 May 11, 2023

(30) Foreign Application Priority Data
Apr. 13, 2020 (JP) ................................ 2020-071624

(51) Int. Cl.
*G01N 27/06* (2006.01)
*G01N 33/28* (2006.01)
*G05B 23/02* (2006.01)

(52) U.S. Cl.
CPC ............. *G01N 27/06* (2013.01); *G01N 33/28* (2013.01); *G05B 23/0254* (2013.01); *G05B 23/0283* (2013.01)

(58) Field of Classification Search
CPC .... G01N 27/06; G01N 33/28; G01N 33/2888; G01N 33/2835; G01N 33/2847;
(Continued)

(56) References Cited

U.S. PATENT DOCUMENTS 4,620,185 A * 10/1986 Plahmer .................. G07C 3/00
73/53.07
6,949,936 B2 * 9/2005 Stone ................. G01N 33/2858
324/633
(Continued)

FOREIGN PATENT DOCUMENTS

CN 1292491 A 4/2001
CN 109073506 A 12/2018
(Continued)

OTHER PUBLICATIONS

S. Keartland and T. L. Van Zyl, "Automating predictive maintenance using oil analysis and machine learning," 2020 International SAUPEC/RobMech/PRASA Conference, Cape Town, South Africa, 2020, pp. 1-6 (Year: 2020).*

Primary Examiner — Daniel R Miller
(74) Attorney, Agent, or Firm — BainwoodHuang (57) ABSTRACT

A technique involves outputting not only the condition of hydraulic oil but also information on failure prediction of equipment by processing in real time. Such a technique utilizes an oil condition sensor attached to the equipment, a parameter calculator that calculates the values of a plurality of parameters indicating the state of the hydraulic oil based on the sensor output of the oil condition sensor and correlation information between the sensor output and the values of a plurality of parameters indicating the state of the hydraulic oil, and failure prediction determiner that predicts equipment failures based on parameter values and identifies and outputs parameters that are inferred as the cause of the failure prediction, and outputs not only the condition of hydraulic oil but also information on failure prediction of the equipment by processing in real time.

7 Claims, 5 Drawing Sheets (58) Field of Classification Search
CPC .......... G01N 33/2858; G01N 33/2876; G01N 27/221; G05B 23/0254; G05B 23/0283; G05B 23/024; F16N 29/00; F16N 29/04; F16N 2200/00; F16N 2200/04; F16N 2200/08; F16N 2200/20; F16N 2260/18; F01M 11/10; F01M 2011/14; F01M 2011/1406; F01M 2011/1413; F01M 2011/1453; F01M 2011/146; F01M 2011/144

See application file for complete search history.

(56) References Cited

U.S. PATENT DOCUMENTS

2009/0315574 A1 12/2009 Akiyama et al.
2019/0156600 A1* 5/2019 Potyrailo ............. G07C 5/0816

FOREIGN PATENT DOCUMENTS

| | | | | |
|---|---|---|---|---|
| CN | 110287980 | A | 9/2019 | |
| CN | 110352350 | A | 10/2019 | |
| CN | 110766059 | A | 2/2020 | |
| DE | 102007042507 | A1 * | 3/2009 | ......... G01N 33/2888 |
| EP | 1085635 | A3 | 10/2003 | |
| EP | 3242118 | A1 | 11/2017 | |
| EP | 3660507 | A1 | 6/2020 | |
| GB | 2306660 | A * | 5/1997 | ........... G01N 27/221 |
| JP | 2001235498 | A | 8/2001 | |
| JP | 2006308515 | A | 11/2006 | |
| JP | 2009002693 | A | 1/2009 | |
| JP | 20160020864 | A | 2/2016 | |
| KR | 20190109505 | A | 9/2019 | |
| KR | 20190002510 | U | 10/2019 | |
| WO | 20170191313 | A1 | 11/2017 | |
| WO | 20190021502 | A1 | 1/2019 | |

* cited by examiner

FAILURE PREDICTION SYSTEM

TECHNICAL FIELD

This invention relates to a failure prediction system.

BACKGROUND ART

The hydraulic oil used in equipment oxidizes and gradually deteriorates with equipment use. Therefore, in order to avoid equipment failure and shortened equipment life, the deterioration state of the hydraulic oil must be properly estimated, and the fluid must be replenished or replaced at the appropriate time.

In order to meet the above requirements, a technology has been disclosed to reduce the time required to determine the degree of deterioration of the hydraulic oil after the hydraulic oil in use in the equipment is sampled (see, for example, patent document 1).

CITATION LIST

Non-Patent Document

Patent Document 1
JP 2016-20864 A.

SUMMARY OF INVENTION

Technical Problem

However, the technology described in the patent document 1 assumes that hydraulic oil is collected while the equipment is in use. As a result, equipment operation must be stopped when collecting hydraulic oil, which affects productivity and work efficiency.

Related to the above problem, assuming that hydraulic oil is collected while the equipment is in use, the condition of the hydraulic oil cannot be evaluated frequently, making it difficult to perform predictive maintenance accurately even if the determination time is reduced.

Furthermore, although the technology described in patent document 1 estimates the degree of deterioration of hydraulic oil, it does not determine equipment failure.

The purpose of the present invention, therefore, is to provide a failure prediction system that outputs not only the state of hydraulic oil but also information on failure prediction of equipment by processing in real time.

Solution of Problem

First Aspect: At least one embodiment of the present invention proposes a failure prediction system of an equipment characterized in comprising: an oil condition sensor attached to the equipment; a parameter calculator to calculate values of the plurality of parameters indicating the state of the hydraulic oil based on a correlation information between a sensor output of the oil condition sensor and the values of the plurality of parameters indicating the state of the hydraulic oil and the sensor output; a failure prediction determiner that predicts a failure of the equipment based on the values of the parameters and identifies and outputs the parameters that are inferred as the cause of the failure prediction.

DESCRIPTION OF EMBODIMENTS

First Embodiment

Hereinafter, a failure prediction system 1 according to a first embodiment of the present invention will be described with reference to FIGS. 1 to 5.

(Configuration of a Failure Prediction System)

The configuration of a failure prediction system 1 according to the first embodiment of the present invention will be described with reference to FIGS. 1 to 3.

Figure 1:
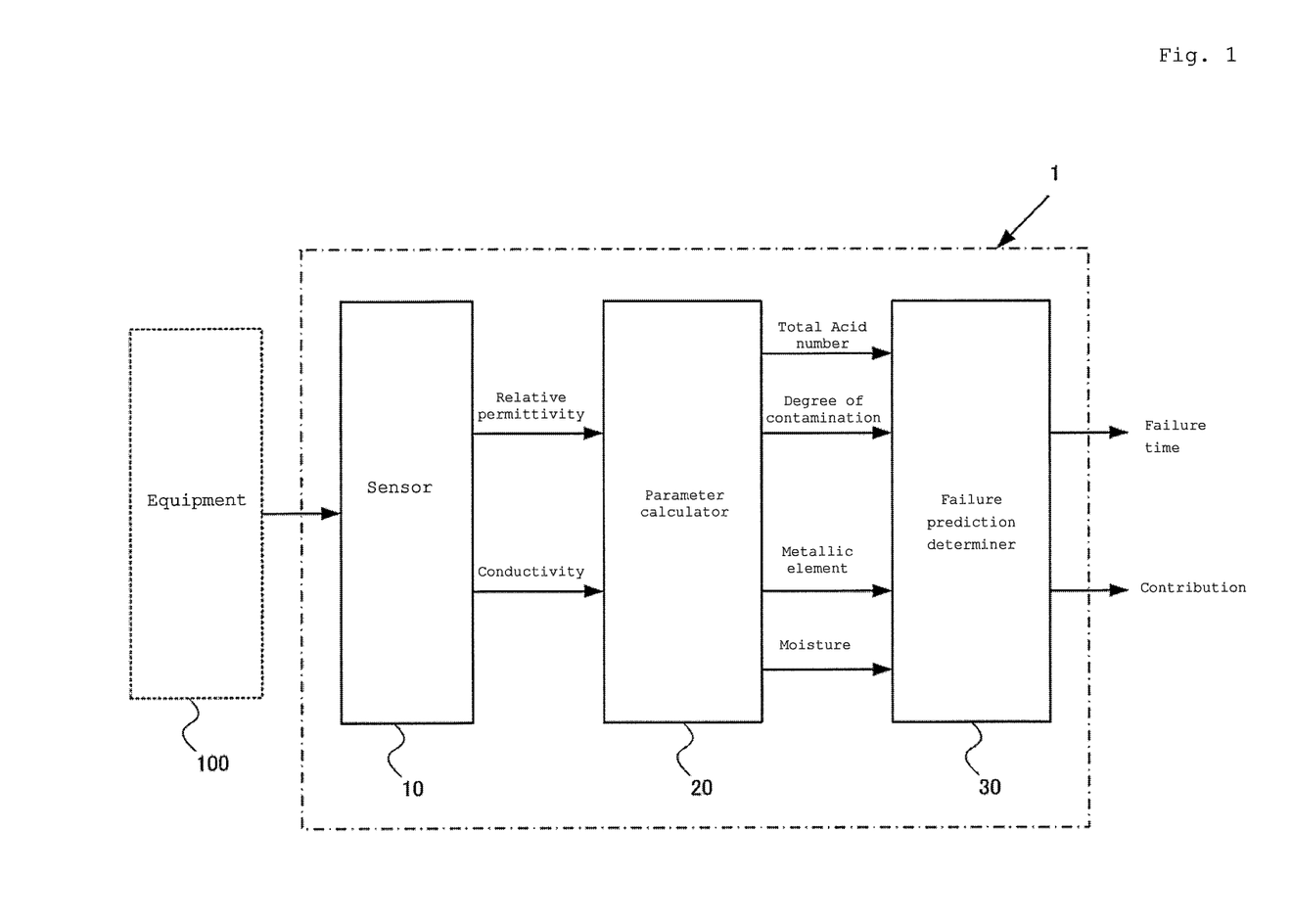
FIG. 1 shows the configuration of failure prediction system according to the first embodiment.

As shown in FIG. 1, the failure prediction system 1 comprises an oil condition sensor 10, a parameter calculator 20, and a failure prediction determiner 30.

The oil condition sensor 10 is an oil condition sensor that detects the oil condition of the hydraulic oil, is mounted so that the sensing member is immersed in the hydraulic oil of the equipment 100 to be sensed, and acquires information including, for example, the relative permittivity and conductivity of the hydraulic oil.

The oil condition sensor 10 is connected to the parameter calculator 20 (described below) wirelessly or via a network, and outputs the information acquired by the oil condition sensor 10 sequentially or at the request of the parameter calculator 20.

The parameter calculator 20 obtains the values of the plurality of parameters indicating the state of the hydraulic oil based on the correlation information between the sensor output of the oil condition sensor 10 and the values of the plurality of parameters indicating the state of the hydraulic oil and the sensor output.

The examples of parameters indicating the condition of the hydraulic oil may be parameters including total acid number, degree of contamination, metallic elements, and moisture.

Here, the parameter calculator 20 may be a stand-alone device or, for example, a server in the cloud.

The failure prediction determiner 30 outputs failure prediction information of equipment 100 in real time from the values of correlated parameters.

Here, the failure prediction determiner 30 inputs the values of correlated parameters, performs machine learning, and outputs failure prediction information of the equipment 100.

For example, as the failure prediction information, the information including the timing of failure and the contribution of parameters indicating the condition of the hydraulic oil can be exemplified.

The failure prediction determiner 30 may be a stand-alone device or, for example, a server in the cloud.

It may be a stand-alone device that combines the failure prediction determiner 30 and the parameter calculator 20, or it may be a server in the cloud, for example.

(Configuration of Parameter Calculator 20)

Figure 2:
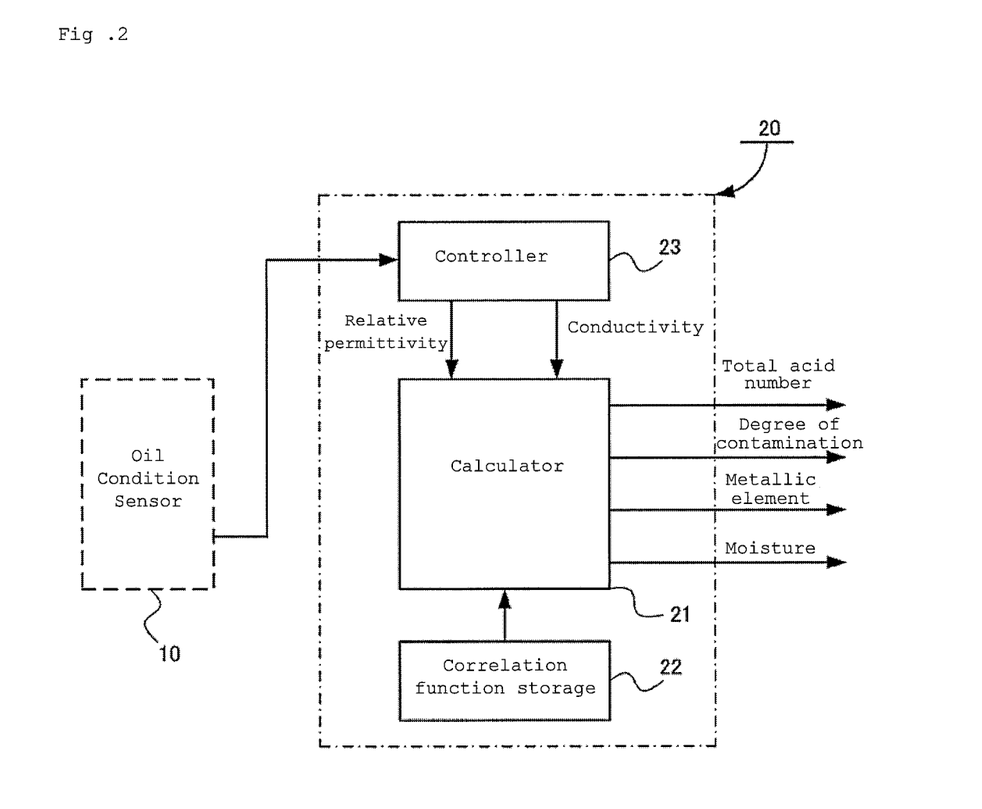
FIG. 2 shows the configuration of the parameter calculator according to the first embodiment.

The parameter calculator 20 consists of a calculator 21, a correlation function storage 22, and a controller 23, as shown in FIG. 2.

The calculator 21 calculates values of parameters indicating the oil condition of the hydraulic oil based on information obtained from the oil condition sensor 10, for example, sensor information including relative permittivity and conductivity, and correlation functions stored in the correlation function storage 22 described below.

The correlation function storage 22 stores correlation functions that indicate the correlation between sensor information obtained from the oil condition sensor 10 and parameters indicating the oil condition of the hydraulic oil.

Correlation functions are calculated by mathematical regression from the vast amount of data collected and include, for example, correlation functions between relative permittivity and total acid number, relative permittivity and degree of contamination, relative permittivity and moisture, conductivity and degree of contamination, conductivity and metallic elements, and conductivity and moisture.

The controller 23 controls the operation of the calculator 21 according to a control program stored in ROM (Read Only Memory) etc.

(Configuration of the Failure Prediction Determiner 30)

Figure 3:
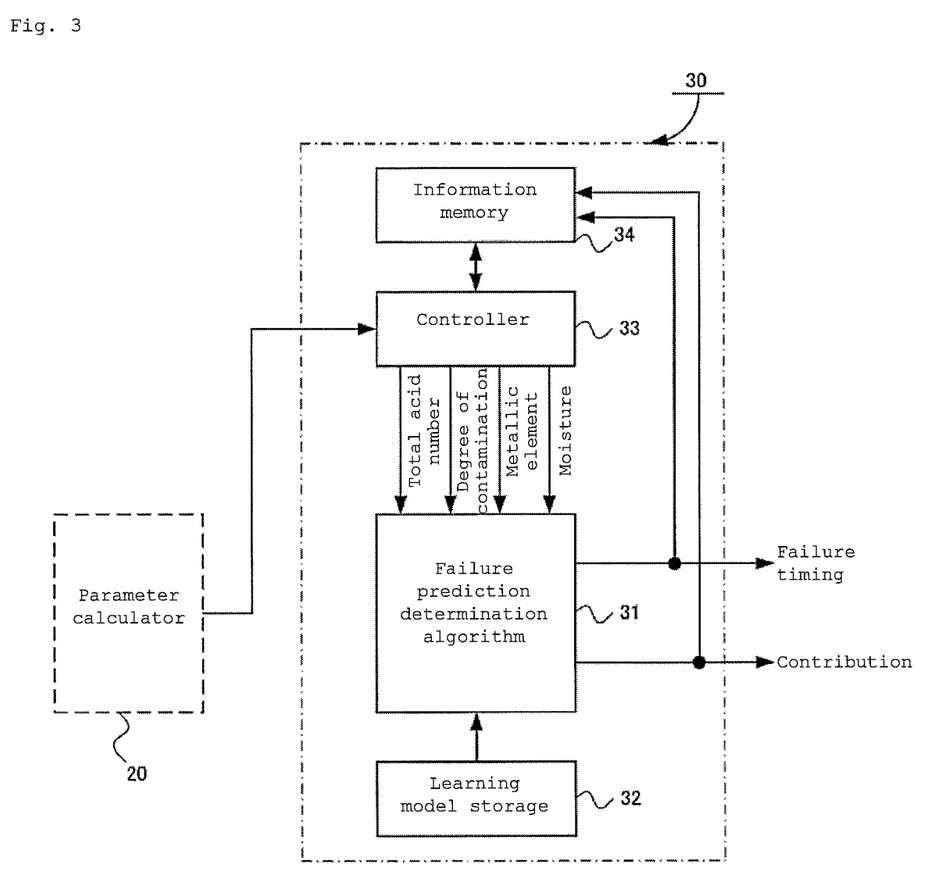
FIG. 3 shows the configuration of the failure prediction determiner according to the first embodiment.

As shown in FIG. 3, the failure prediction determiner 30 comprises a failure prediction determination algorithm 31, a learning model storage 32, a controller 33, and an information memory 34.

The failure prediction determination algorithm 31 is an algorithm for performing machine learning in the failure prediction determiner 30, and it takes as input the values of the parameters indicating the oil condition of the hydraulic oil calculated in the parameter calculator 20, performs machine learning using the learning model described below, and outputs failure prediction information including failure timing and contribution of the parameters indicating the oil condition of the hydraulic oil, for example, and corresponding messages to prevent failure.

As an example of the failure prediction determination algorithm 31, a boosting that forms a decision tree structure can be exemplified.

The learning model storage 32 stores learning models generated in advance. Here, the learning model is data from which rules and patterns (outputs) are learned based on input data.

The controller 33 controls the operation of the failure prediction determiner 30 according to a control program stored in ROM (Read Only Memory) etc.

In addition, the ROM and other memory elements of the controller 33 store corresponding messages etc. in response to failure prediction information to prevent failures before they occur.

The controller 33 causes all of the equipment 100 to perform failure prediction determination. In other words, the controller 33 causes the same model and the same period of use of the equipment 100 to perform the failure prediction determination.

The information memory 34 stores a database linking the information input from the parameter calculator 20 and the failure prediction information output from the failure prediction determination algorithm 31.

(Processing of Failure Prediction System)

Figure 4:
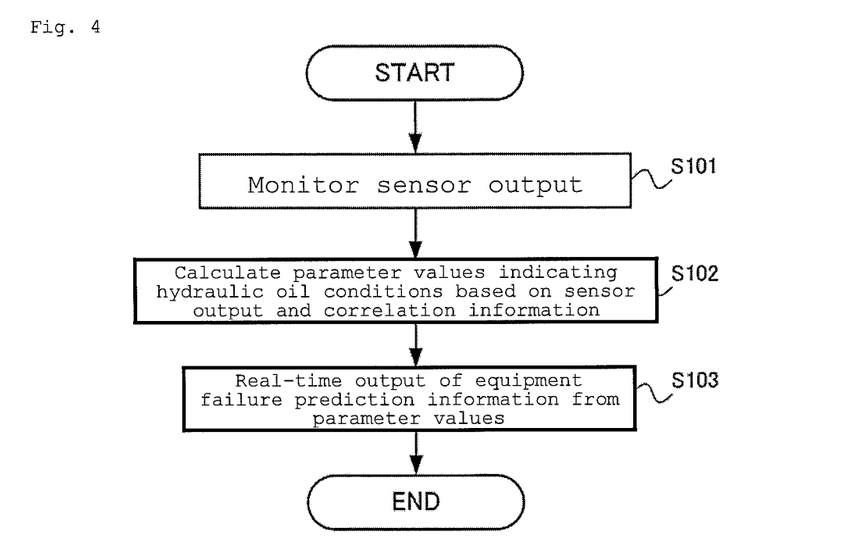
FIG. 4 is the flowchart showing the process of the failure prediction system according to the first embodiment.

Processing of the failure prediction system according to the first embodiment of the present invention will be described with reference to FIGS. 4 and 5.

The controller 23 of the parameter calculator 20 monitors, for example, the output from the oil condition sensor 10 at predetermined time intervals, and outputs sensor information obtained from the oil condition sensor 10, including, for example, relative permittivity and conductivity, to the calculator 21 (step S101).

The calculator 21 of the parameter calculator 20 calculates the value of the parameter indicating the oil condition of the hydraulic oil based on the information input from the controller 23, for example, sensor information including relative permittivity and conductivity, and the correlation function stored in the correlation function storage 22 described below (step S102).

Figure 5:
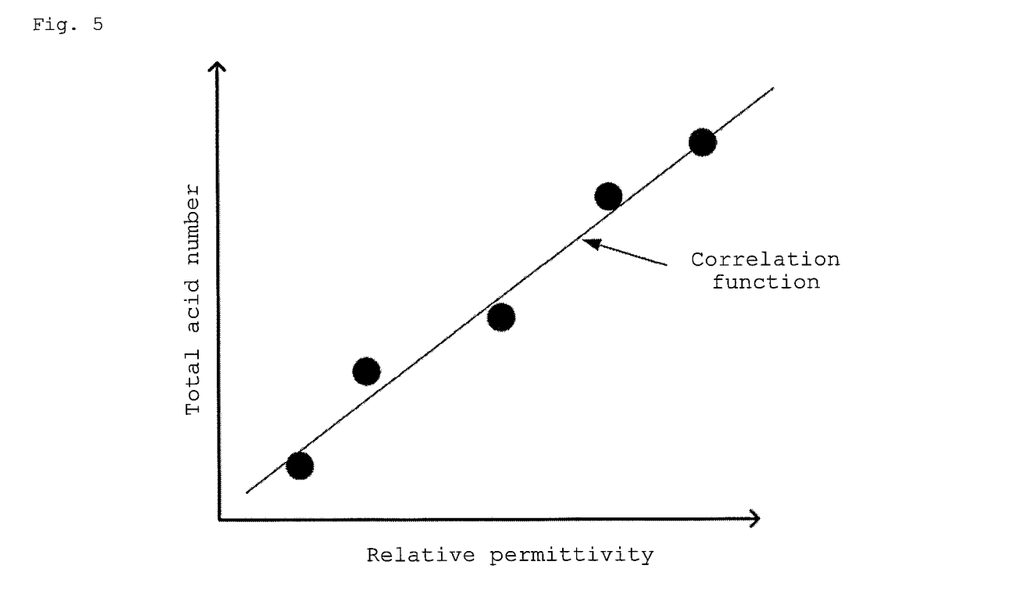
FIG. 5 shows the correlation stored in the correlation function storage of the parameter calculator according to the first embodiment.

For example, the correlation function storage 22 stores correlation functions between relative permittivity and degree of contamination, correlation functions between relative permittivity and moisture, correlation functions between conductivity and degree of contamination, correlation functions between conductivity and metallic elements, correlation functions between conductivity and moisture, etc., including the correlation function between permittivity and total acid number as shown in FIG. 5.

The calculator 21 calculates the values of parameters indicating the oil condition of the hydraulic oil, for example, total acid number, degree of contamination, metallic elements, and moisture, based on sensor information including relative permittivity and conductivity and correlation functions stored in the correlation function storage 22, and outputs them to the failure prediction determiner 30.

The controller 33 of the failure prediction determiner 30 incorporates the calculation results of the parameter calculator 20 into the failure prediction determination algorithm 31.

The failure prediction determination algorithm 31 takes as input the values of parameters indicating the oil condition of the hydraulic oil calculated in the parameter calculator 20 and executes machine learning using a learning model to display on a display (not shown) or output to a user terminal or the like in real time, for example, failure prediction information including failure timing, contribution of parameters indicating the oil condition, and corresponding messages etc. for preventing failures (step S103).

The information output from the parameter calculator 20 and the failure prediction information output from the failure prediction determination algorithm 31 are stored in the information memory 34 in the form of a database.

(Effect)

As explained above, in the failure prediction system 1 according to this embodiment, based on the sensor output of the oil condition sensor 10 attached to the equipment 100 and the correlation information between the sensor output and the values of multiple parameters indicating the state of the hydraulic oil, the parameter calculator 20 obtains the values of multiple parameters indicating the state of the hydraulic oil, and the failure prediction determiner 30 predicts a failure of the equipment 100 from the parameter values, identifies parameters that are speculated as the cause of failure prediction, and outputs failure prediction information in real time.

Therefore, the oil condition of the hydraulic oil and the failure of the equipment 100 can be monitored in real time based on the sensor outputs of the oil condition sensor 10 attached to the equipment 100 and the correlation information between the values of multiple parameters indicating the condition of the hydraulic oil and the sensor outputs, which enables early determination of when to replace the hydraulic oil appropriately and the failure of the equipment 100.

In the failure prediction system 1 according to this embodiment, the parameter calculator 20 obtains the values of multiple parameters indicating the state of the hydraulic oil, and the failure prediction determiner 30 predicts failure of the equipment 100 from the values of the parameters, identifies the parameters that are inferred as the cause of the failure prediction, and outputs failure prediction information in real time.

In other words, since the failure prediction system 1 notifies users of failure prediction information after predicting the condition of hydraulic oil, the basis of failure prediction information can be presented to users based on the prediction results of hydraulic oil conditions.

In addition, since the failure prediction system 1 according to this embodiment displays on a display (not shown) or outputs to a user terminal or the like in real time information including the time of failure, the contribution of parameters indicating the state of the hydraulic oil, and a corresponding message to prevent failure, it can prompt the user to act quickly.

The parameter calculator in the failure prediction system 1 according to this embodiment obtains the values of the parameters from the sensor outputs of the oil condition sensors using the first learning data generated by machine learning with the previously measured parameter values as teacher data.

In other words, the parameter calculator 20 in the failure prediction system 1 according to this embodiment stores, for example, a correlation function between sensor outputs mathematically calculated based on collected data and parameters indicating the state of hydraulic oil, and uses first learning data generated by machine learning with previously measured parameter values as teacher data to obtain the values of parameters from the sensor outputs of the oil condition sensors.

Therefore, it is possible to predict how the values of parameters indicating the state of the hydraulic oil will change relative to changes in sensor output values due to the cumulative usage time of the equipment 100 and other factors.

The failure prediction determiner in the failure prediction system 1 according to this embodiment identifies and outputs said parameters that are inferred as causes of failure prediction of equipment from the values of the parameters calculated by the parameter calculator using a second learning model generated by machine learning, with the objective variable being whether the equipment is in a failed state or not, or in a state that is predictive of failure, and the parameter being an explanatory variable.

That is, for example, the failure prediction determiner in the failure prediction system 1 according to this embodiment identifies and outputs said parameters that are inferred as causes of failure prediction of equipment from the values of parameters calculated by the parameter calculator based on a second learning model generated by machine learning, using as objective variables whether the equipment is in a failed state or not, or whether it is in a state that is predicted to fail, and parameters as explanatory variables.

Therefore, it is possible to output highly accurate information on failure prediction of equipment in a short period of time.

The controller 33 in the failure prediction system 1 according to this embodiment will have the failure prediction determination performed for all equipment 100, i.e., for devices of the same model and with the same period of use.

In general, it is expected that similar failure prediction trends will appear for the same model of equipment 100, but the failure prediction trends differ in the contribution of parameters indicating the condition of the hydraulic oil, depending on the user's usage.

Therefore, in the failure prediction system 1 according this embodiment, by having the failure prediction determination performed on, for example, equipment 100 of the same model and with the same period of use, the failure prediction information for each equipment 100 can be reported to the user.

A function to generate a learning model may be added to the failure prediction system 1, and the learning model may be generated by the information used in the process of acquiring failure prediction information and the failure prediction information, and the learning model used in the process of acquiring failure prediction information may be updated.

Thus, the accuracy of generating failure prediction information in the failure prediction system 1 can be improved by updating the learning model using the newly obtained information.

Second Embodiment

Figure 6:
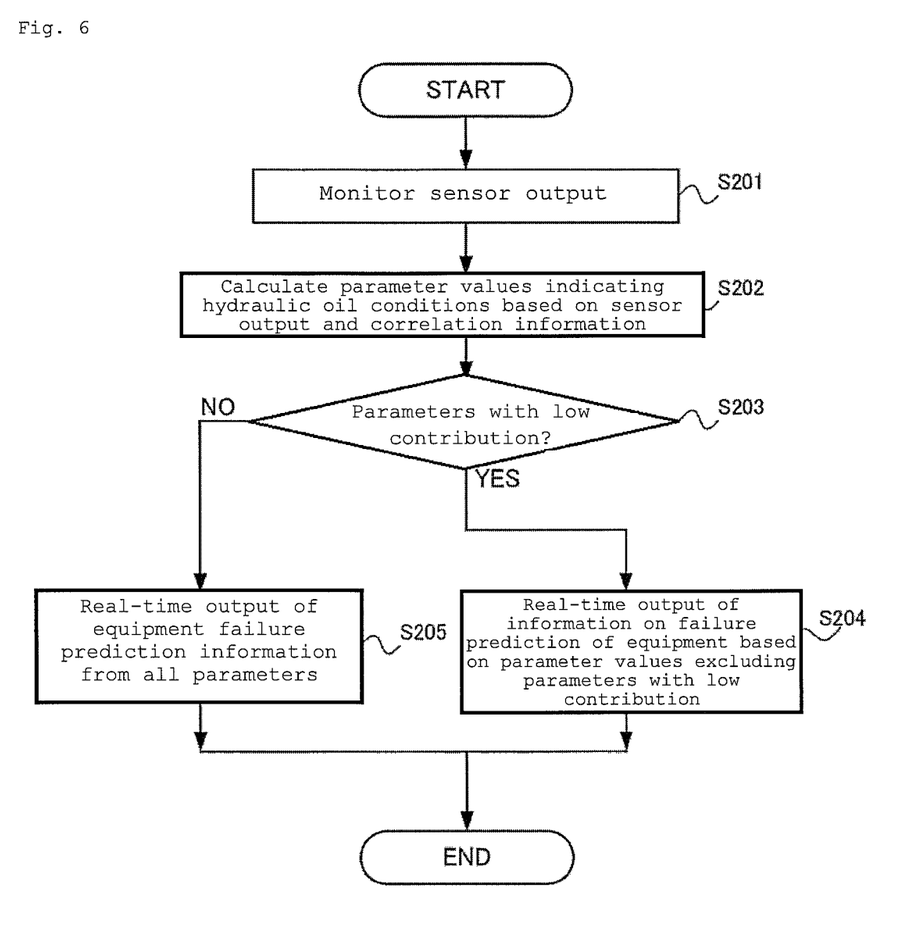
FIG. 6 is the flowchart showing the process of the failure prediction system according to the second embodiment.

Hereinafter, the failure prediction system 1A according to the second embodiment of the invention will be described with reference to FIG. 6.

(Configuration of Failure Prediction System 1A)

The configuration of the failure prediction system 1A according to the second embodiment of the invention will be described.

The failure prediction system 1A according to this embodiment comprises an oil condition sensor 10, a parameter calculator 20, and a failure prediction determiner 30A.

Detailed descriptions of the components with the same symbols as in the first embodiment are omitted, since they have the same functions.

The failure prediction determiner 30A outputs failure prediction information of equipment 100 in real time from the values of correlated parameters.

The failure prediction determiner 30A does not perform machine learning on the next and subsequent contribution for parameters whose contribution is lower than the set value.

(Configuration of Failure Prediction Determiner 30A)

The failure prediction determiner 30A comprises a failure prediction determination algorithm 31, a learning model storage 32, a controller 33A, and an information memory 34.

Detailed descriptions of the components with the same symbols as in the first embodiment are omitted, since they have the same functions.

The controller 33A controls the operation of the failure prediction determiner 30A according to a control program stored in ROM (Read Only Memory) etc.

The controller 33A detects parameters whose contribution is lower than the set value based on the database linking the information input from the parameter calculator 20 and the failure prediction information output from the failure prediction determination algorithm 31 stored in the information memory 34, and controls the failure prediction determiner 30A not to perform machine learning on the contribution from the next time onward for the parameter in question.

(Processing of Failure Prediction System 1A)

Processing of the failure prediction system 1A according to the second embodiment of the present invention will be described with reference to FIG. 6.

The controller 23 of the parameter calculator 20, for example, monitors the output from the oil condition sensor 10 at predetermined time intervals and outputs sensor information obtained from the oil condition sensor 10, including, for example, relative permittivity and conductivity, to the calculator 21 (step S201).

The calculator 21 of the parameter calculator 20 calculates values of parameters indicating the oil condition of the hydraulic oil based on information input from the controller 23, for example, sensor information including relative permittivity and conductivity, and correlation functions stored in the correlation function storage 22 described below (step S202).

The controller 33A of the failure prediction determiner 30A determines the presence or absence of parameters whose contribution is lower than a set value based on a database stored in the information memory 34 that links the information input from the parameter calculator 20 and the failure prediction information output from the failure prediction determination algorithm 31 (step S203).

At this time, if it is determined that there is no parameter in the database whose contribution is lower than the set value ("NO" in step S203), the controller 33A of the failure prediction determiner 30A executes control so that all calculation results of the parameter calculator 20 are incorporated into the failure prediction determination algorithm 31, wherein the failure prediction determination algorithm 31 takes as input the values of parameters indicating the oil state of the hydraulic oil calculated in the parameter calculator 20 and executes machine learning using a learning model to display on a display (not shown) or output to a user terminal or the like in real time, for example, failure prediction information including failure timing, contribution of parameters indicating the condition of the hydraulic oil, and corresponding messages for preventing failures (step S205).

On the other hand, if it is determined that there is parameter in the database whose contribution is lower than the set value ("YES" in step S203), the controller 33A of the failure prediction determiner 30A executes control so that the calculated results of the parameters excluding the calculation results of the parameters whose contribution is lower than the set value among the calculation results of the parameter calculator 20 are incorporated into the failure prediction determination algorithm 31, wherein the failure prediction determination algorithm 31 takes as input the values of parameters indicating the oil state of the hydraulic oil calculated in the parameter calculator 20 and executes machine learning using a learning model to display on a display (not shown) or output to a user terminal or the like in real time, for example, failure prediction information including failure timing, contribution of parameters indicating the oil condition, and corresponding messages for preventing failures (step S204).

(Effect)

As explained above, the controller 33A of the failure prediction determiner 30A in the failure prediction system 1A according to this embodiment determines the presence or absence of parameters whose contribution is lower than a set value based on a database stored in the information memory 34 that links the information input from the parameter calculator 20 and the failure prediction information output from the failure prediction determination algorithm 31, and when it is determined that there is a parameter in the database whose contribution is lower than the set value ("YES" in step S203), it executes control so that the calculated results of the parameters excluding the calculation results of the parameters whose contribution is lower than the set value among the calculation results of the parameter calculator 20 are incorporated into the failure prediction determination algorithm 31, wherein the failure prediction determination algorithm 31 takes as input the values of parameters indicating the oil state of the hydraulic oil calculated in the parameter calculator 20 and executes machine learning using a learning model to display on a display (not shown) or output to a user terminal or the like in real time, for example, failure prediction information including failure timing, contribution of parameters indicating the oil condition, and corresponding messages for preventing failures.

Therefore, if there is a parameter whose contribution is lower than a set value based on the database linking the information input from the parameter calculator 20 and the failure prediction information output from the failure prediction determination algorithm 31 stored in the information memory 34, the processing load of the failure prediction determiner 30A can be reduced.

(Variation 1)

In the first and second embodiments, the parameter calculator 20 calculates the value of the parameter indicating the oil condition of the hydraulic oil based on the information obtained from the oil condition sensor 10, for example, sensor information including relative permittivity and conductivity, and a correlation function calculated by mathematical regression from a vast amount of data stored in the correlation function storage 22 described below.

However, the parameter calculator 20 may calculate the value of the parameter from the correlation between the sensor information including relative permittivity and conductivity obtained from a vast amount of data using a specific algorithm and the value of the parameter indicating the oil condition of the hydraulic oil.

In this way, the values of parameters can be calculated with a high degree of accuracy even when the relationship between sensor information including relative permittivity and conductivity and the values of parameters indicating the oil condition of the hydraulic oil have a relationship that cannot be expressed by a function.

In Variation 1, it is exemplified that different algorithms are applied to the parameter calculator 20 and the failure prediction determiner 30 and 30A to perform failure prediction determination. However, under the condition that it is limited to certain specific data, such as data with high dielectric constant, for example, the parameter calculator 20 and the failure prediction determiner 30 and 30A may be operated using one algorithm.

In the first and second embodiments, the application of a machine learning classification algorithm to the failure prediction determiners 30 and 30A is exemplified, but a theory-based or rule-based algorithm may also be applied.

(Variation 2)

The failure prediction determiner 30 may perform machine learning of the contribution even if the equipment 100 is the same model as the equipment 100 for which machine learning of the contribution of the parameters indicating the condition of the hydraulic oil has been performed so far.

In other words, even for the same model of equipment, different usage conditions, such as its usage method and operating environment, will result in different contributions, and different failure modes can be expected.

Therefore, even if the equipment is of the same model, the user can be notified of the true failure prediction information for that equipment by performing contribution machine learning.

The failure prediction systems 1 and 1A of the present invention can be realized by recording the processes of the failure prediction systems 1 and 1A on a recording medium readable by a computer system and having the program recorded on this recording medium read and executed by the failure prediction systems 1 and 1A. The computer system here includes hardware such as an OS and peripheral devices.

"Computer system" shall include the homepage provision environment (or display environment) if the WWW (World Wide Web) system is used. The above program may be transmitted from a computer system storing this program in a memory device or the like to another computer system via a transmission medium or by transmission waves in a transmission medium. Here, "transmission medium" for transmitting the program refers to a medium that has the function of transmitting information, such as a network (communication network) such as the Internet or a communication channel (communication line) such as a telephone line.

The above programs may also be those that can be used to realize some of the aforementioned functions. Furthermore, it may be a so-called difference file (difference program), which can realize the aforementioned functions in combination with a program already recorded in the computer system.

Although the above embodiments of this invention have been described in detail with reference to the drawings, specific configurations are not limited to these embodiments, and includes designs and the like within a range that does not deviate from the gist of the present invention.

According to the above failure prediction system, it is possible to output not only the condition of hydraulic oil but also information on failure prediction of equipment through real-time processing.

DESCRIPTION OF THE REFERENCE NUMERALS

1; Failure prediction system
1A; Failure prediction system
10; Oil condition sensor
20; Parameter calculator
21; Calculator
22; Correlation function storage
23; Controller
30; Failure prediction determiner
30A; Failure prediction determiner
31; Failure prediction determination algorithm
32; Learning model storage
33; Controller
33A; Controller
34; Information memory
100; Equipment

The invention claimed is:

1. A failure prediction system of an equipment, comprising:
  an oil condition sensor that outputs information including at least one of a relative permittivity and a conductivity of hydraulic oil, and attached to the equipment;
  a parameter calculator formed by processing circuitry running parameter-calculating software read from memory to calculate values of a plurality of parameters indicating a state of the hydraulic oil based on: (1) correlation information between a pre-collected sensor output of the oil condition sensor and the values of the plurality of parameters indicating the state of the hydraulic oil and (2) the information; and
  a failure prediction determiner formed by the processing circuitry running failure-prediction software read from the memory to provide a failure prediction that predicts a failure of the equipment based on the values of the plurality of parameters calculated in the parameter calculator and identifies and outputs parameters that are inferred as causes of the failure prediction;
  wherein the failure prediction determiner identifies and outputs the parameters that are inferred as the causes of the failure prediction of the equipment from the values of the plurality of parameters calculated by the parameter calculator using a second learning model generated by machine learning, with whether the equipment is in a failed state or in a state of failure prediction as an objective variable, and the parameters that are inferred as the causes of the failure prediction as explanatory variables; and
  wherein the failure prediction determiner calculates and outputs a contribution of the parameters that are inferred as the causes of the failure prediction using an algorithm of a decision tree structure as the second learning model.

2. The failure prediction system of the equipment according to claim 1, wherein the parameter calculator calculates the values of the plurality of parameters from the information output by the oil condition sensor using a first learning model generated by machine learning with a previously measured value of the parameter as teacher data.

3. The failure prediction system of the equipment according to claim 1, wherein the failure prediction determiner does not perform a process of calculating a contribution, from a next time the failure prediction determiner calculates the contribution and onward, for a parameter with a contribution lower than a preset value.

4. The failure prediction system of the equipment according to claim 1, wherein the oil condition sensor outputs electrical characteristics of the hydraulic oil, including the relative permittivity and the conductivity of the hydraulic oil, wherein the parameter calculator calculates parameters for total acid number, degree of contamination, metallic elements, and moisture based on the relative permittivity and the conductivity.

5. The failure prediction system of the equipment according to claim 1, wherein the parameter calculator calculates the values of the plurality of parameters from a correlation between the information of the oil condition sensor including the relative permittivity and the conductivity obtained from collected data using a specific algorithm and the values of the plurality of parameters indicating the state of the hydraulic oil and the sensor output.

6. The failure prediction system of the equipment according to claim 1, wherein the failure prediction determiner is constructed and arranged to perform failure prediction determination for multiple equipment of a same model and with a same period of use.

7. The failure prediction system of the equipment according to claim 1, further comprising:
  a learning model generator formed by the processing circuitry running learning-model-generating software read from the memory to generate a third learning model using the information used in the process of acquiring failure prediction information and the failure prediction information,
wherein the failure prediction determiner updates the second learning model to the third learning model and performs a failure prediction determination.

* * * * *